(12) United States Patent
Cowe

(10) Patent No.: US 9,168,339 B2
(45) Date of Patent: Oct. 27, 2015

(54) INJECTION DEVICE

(75) Inventor: Toby Cowe, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 0 days.

(21) Appl. No.: 14/002,847

(22) PCT Filed: Mar. 2, 2012

(86) PCT No.: PCT/GB2012/050470
§ 371 (c)(1),
(2), (4) Date: Sep. 3, 2013

(87) PCT Pub. No.: WO2012/117255
PCT Pub. Date: Sep. 7, 2012

(65) Prior Publication Data
US 2013/0345642 A1 Dec. 26, 2013

Related U.S. Application Data

(60) Provisional application No. 61/448,438, filed on Mar. 2, 2011.

(30) Foreign Application Priority Data

Mar. 2, 2011 (GB) .................................. 1103557.3

(51) Int. Cl.
A61M 5/20 (2006.01)
A61M 5/315 (2006.01)

(52) U.S. Cl.
CPC ............. *A61M 5/31535* (2013.01); *A61M 5/20* (2013.01); *A61M 5/3157* (2013.01); *A61M 5/2033* (2013.01); *A61M 2005/206* (2013.01); *A61M 2005/208* (2013.01); *A61M 2205/581* (2013.01); *A61M 2205/582* (2013.01); *A61M 2205/583* (2013.01)

(58) Field of Classification Search
USPC ......... 604/134, 136, 141, 154, 191, 207, 211, 604/82, 131, 208; 222/43
See application file for complete search history.

(56) References Cited

U.S. PATENT DOCUMENTS

| 5,271,527 A | 12/1993 | Haber et al. |
| 6,454,743 B1 | 9/2002 | Weber |
| 2006/0258990 A1 | 11/2006 | Weber |

FOREIGN PATENT DOCUMENTS

| CH | 700 404 | 8/2010 |
| GB | 2460398 | 12/2009 |
| WO | 2004/108194 | 12/2004 |

(Continued)

OTHER PUBLICATIONS

International Search Report dated Jul. 3, 2012, corresponding to PCT/GB2012/050470.

(Continued)

*Primary Examiner* — Scott Medway
(74) *Attorney, Agent, or Firm* — Young & Thompson

(57) ABSTRACT

In an injection device a rotary indicator element (20) indexes angularly between a pre-firing position to an injection complete position to create a visual and audible/tactile signal as the drive plunger (28) arrives at or near its fired position. The indicator element (20) has a saw tooth profile which cooperates with respective abutments (34, 40) on the plunger and a housing part of the device to control and energise indicator movement.

9 Claims, 10 Drawing Sheets

(56) References Cited

FOREIGN PATENT DOCUMENTS

| WO | 2005/009515 | 2/2005 |
|----|-------------|--------|
| WO | 2005/070481 | 8/2005 |
| WO | 2007/132353 | 11/2007 |
| WO | 2008/005315 | 1/2008 |
| WO | 2009/141650 | 11/2009 |
| WO | 2010/035056 | 4/2010 |
| WO | 2010/035057 | 4/2010 |
| WO | 2010/035059 | 4/2010 |
| WO | 2011/043714 | 4/2011 |
| WO | 2011/123024 | 10/2011 |
| WO | 2012/022810 | 2/2012 |

OTHER PUBLICATIONS

British Search Report dated Jun. 10, 2011, corresponding to GB 1103557.3.

INJECTION DEVICE

BACKGROUND OF THE INVENTION

1. Field of the Invention

This invention relates to injection devices and in particular, but not exclusively, to reusable autoinjector devices comprising a housing into which a disposable syringe may be inserted to effect the injection and then removed and replaced as required for the next injection.

2. Description of the Related Art

It is a common requirement that autoinjectors signal to the user when the injection is complete by means of an 'injection complete' signal. The term 'injection complete' is used to refer to a condition in which a satisfactory delivery of the drug has been achieved. It is also desirable that this indication is not only visual but also audible and/or tactile, to provide confirmation to the user when injection site is out of sight, or would require some straining to see, for example in the buttocks or upper arm.

It is desirable that at least some of the energy required to generate the audible signal is stored in an energy store associated with an indicator element so that a fast impact energetic movement can be released, that is essentially independent of the actual speed of plunger movement. Moreover it is desirable to provide an indicator arrangement which resets automatically for each injection cycle.

BRIEF SUMMARY OF THE INVENTION

Accordingly, in one aspect, this invention provides an injection device including an injection complete indicator for providing a kinetic impact indication, the device including:

a housing;

a plunger moveable in said housing between cocked and fired positions under the influence of a plunger drive source;

an indicator element biased towards an injection complete indicating position by an indicator bias;

a hold-release arrangement responsive to arrival of said plunger at or near its fired position to release said indicator element for movement under the influence of said indicator bias to move to said injection complete indicating position to impact a stop to create said kinetic impact.

By this arrangement, the energy to create the kinetic impact may be stored in the indicator bias which means that, once the indicator element is released its movement is generally independent of the plunger, which allows considerable flexibility in the design of the extent of movement, and energy delivered by the indicator.

Preferably said indicator element also provides a visual indication.

Conveniently, as said plunger moves towards its fired position, it energises said indicator bias. There are numerous ways which the bias may be energised, but in one arrangement, said plunger and said indicator element may have co-operating surfaces which engage to move the indicator element with the plunger during a part of the plunger stroke, thereby to energise said indicator bias. The hold-release arrangement may include a hold surface that co-operates with a complimentary surface on said indicator element to prevent movement thereof to said injection complete indicating position during energisation of said indicator bias. In this way, the energy tapped from the drive source is spread over a significant portion of the stroke of movement of the plunger so as to reduce the effect on the plunger movement. This allows an energy charging cycle in which charging is done slowly over an extended portion of the stroke, and discharging is done very quickly in a snap action.

In this arrangement, as said plunger arrives near or at its fired position, the plunger may move the complimentary surface on the indicator element out of co-operation with said hold surface, thereby releasing the indicator element for movement.

Preferably the indicator element moves angularly to its injection complete indicating position, optionally with an amount of longitudinal movement.

Preferably the indicator bias biases the indicator element linearly in a rearward direction generally opposed to that of the plunger as it moves towards its fired position and co-operating surfaces of said plunger and said indicator element are operable to act in a cammed manner to convert relative linear movement therebetween into angular movement of said indicator element upon release.

Preferably, the co-operating surfaces comprise an ear on said plunger and a repeating profile on said indicator element, the repeating profile comprising a plurality of ramp surfaces alternating with rising edge surfaces arranged such that a rising edge surface is adapted to impact a side of said ear as said indicator element reaches its injection complete indicating position.

Preferably said hold surface is provided on an element that includes a cam face that co-operates with one of said ramp surfaces on said indicator element to rotate the indicator element to a pre-firing position under the influence of said indicator bias as said drive plunger is returned to a cocked position.

In another aspect, this invention provides an injection device including an injection complete indicator, the device including:

a housing;

a plunger movable in said housing between cocked and fired positions under the influence of a plunger drive source;

an indicator element movable between a pre-firing position and an injection complete position;

the device being arranged such that, upon firing, as the plunger nears or reaches the end of its operating stroke, the indicator element is caused to move to its injection complete position and wherein subsequent re-cocking of the plunger returns said indicator element to its pre-firing position.

Whilst the invention has been described above it extends to any combination of the inventive features disclosed herein or in the following description or drawings.

BRIEF DESCRIPTION OF THE DRAWINGS

The invention may be performed in various ways and, by way of example only, an embodiment thereof will now be described, reference being made to the accompanying drawings in which.

DETAILED DESCRIPTION OF THE PREFERRED EMBODIMENTS

Figure 1:
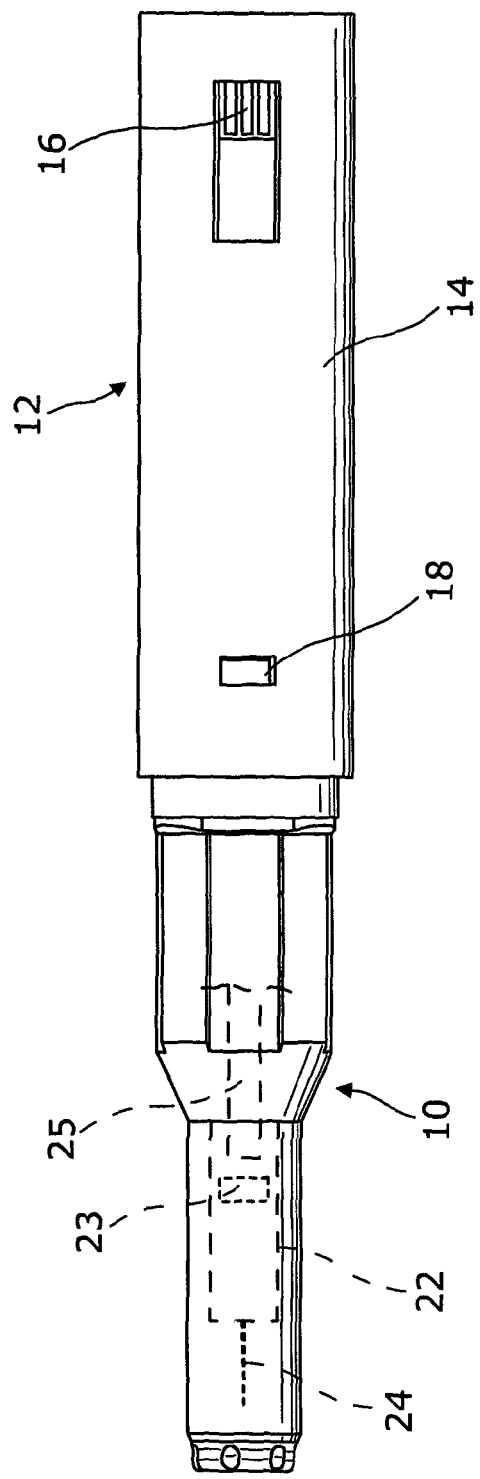
FIG. 1 is a general perspective view of an autoinjection device in accordance with this invention.

Referring initially to FIG. 1, a preferred embodiment of autoinjector comprises a separable body comprising a front body assembly 10 screwed or otherwise releasably coupled to a rear body 12 having an outer slideable cover 14. The device is designed to be reusable with the user separating the front and rear body assembly, cocking a drive mechanism contained in the rear body assembly, inserting or replacing a syringe 22 housed in the front body assembly and connecting the front and rear body assemblies together ready for use. This is similar to a well known Autoject® II device and as described in WO2004/108194. As in the arrangement of WO2004/108194, the cover is biased rearwardly to a position in which it interlocks with a trigger 16 to prevent actuation thereof. The cover 14 also has two diametrically opposed windows 18 through which an indicator sleeve 20 is visible and which moves to change colour on satisfactory completion of an injection.

In order to operate the device, the user grasps the cover 14 and presses the front end of the front body assembly 10 against the injection site, thus shifting the cover forwardly to release the mechanical interlock. On firing the trigger, the drive mechanism inside the rear body housing moves a drive plunger forwardly which is in contact with the syringe plunger 25 and this initially advances the syringe 22 so that its needle 24 penetrates the injection site, and thereafter the plunger moves the syringe piston 23 to expel a dose. Upon nearing or reaching the forward end of its stroke, the plunger releases the indicator sleeve 20 which rotates to change colour under the window 18 and to create an internal impact which provides an audible and tactile signal. On removing the device from the injection site the reaction force is removed and so the cover 14 shifts rearwardly on the rear body to interlock with the trigger 16.

Because of the accumulated tolerances on the syringe (typically of glass) it is known that there is a variation in the forwardmost position of the plunger and so the injection complete position is usually determined to be a short distance behind the final, forwardmost position of the plunger.

Figure 2:
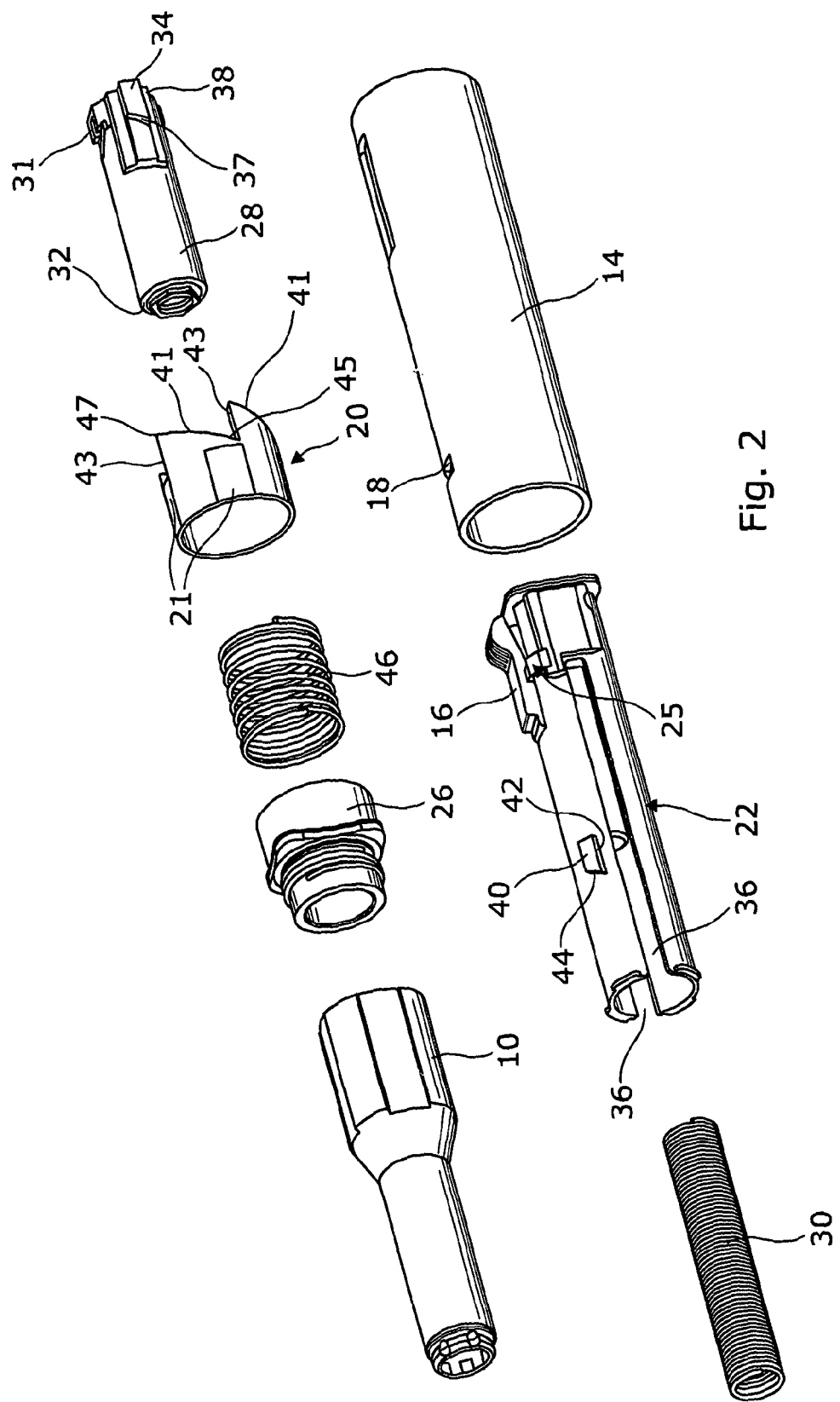
FIG. 2 is an exploded view of the rear body assembly with the syringe removed.

Referring now to FIGS. 2-4, the rear body assembly will be described in more detail. In FIGS. 3 and 4, the rear body assembly 12 is shown in side and perspective views respectively, with a portion of the cover 14 cut away to reveal the inner workings of the assembly. In this arrangement, the cover 14 is slideably mounted around the outside of an inner body housing 22 of generally cylindrical form. At its rear end, the trigger 16 is secured by means of an integral fitting 24 which clips over the rear end of the inner body housing and supports the trigger for resilient rocking release movement. At the forward end of the inner body housing 22 is secured an externally threaded collar fitting 26 which screws into a threaded bore in the rear end of the front body assembly 10. Slideably disposed within the inner body housing 22 is a drive plunger 28 which is urged forwardly by a main drive spring 30 acting between the plunger and a rear inner wall of the rear body assembly. The plunger 28 has a forward end face 32 (visible in FIGS. 3(b) to (h)) which is designed to engage the plunger 25 of a syringe 22. The drive plunger 28 has at its rear end a latch surface 31 which latches with a corresponding latch surface (not shown) on the forward underside end of the trigger 16 which holds the plunger in its rearward, cocked position against the force of the main spring 30. The drive plunger 28 has a pair of transverse ears 34 that extend through opposed longitudinal slots 36 in the wall of the inner body housing 22. Each ear 34 has an inclined cam surface 37 and a longitudinally extending impact surface 38. Towards the front end of the slot and angularly spaced therefrom in a counter-clockwise direction when viewed from the front end, are two diametrically opposed body stops 40 each of which defines a longitudinally extending hold surface 42 and a cam surface 44.

The plunger ears 34 and the body stops 40 each co-operate with a circumferentially extending, rearwardly facing saw tooth profile on the rear of the indicator sleeve 20 which is slideably and rotatably mounted on the front end of the inner body housing 22. The saw tooth profile in this example is made up of four linear ramp surfaces 41 each subtending an angle of 90°, and four axial rising edges 43, with valleys 45 and peaks 47 being defined where the ramps meet the rising edges 43. The indicator sleeve 20 is biased rearwardly by a compression spring 46 that acts between a forward facing inner shoulder of the indicator 20 and the rearward facing edge of the collar fitting 26. The compression spring 46 is much weaker than the main spring 30. The indicator sleeve carries coloured patches 21 equispaced at 90° around the sleeve which provide a visual indication of when the injection is complete.

Figure 3A:
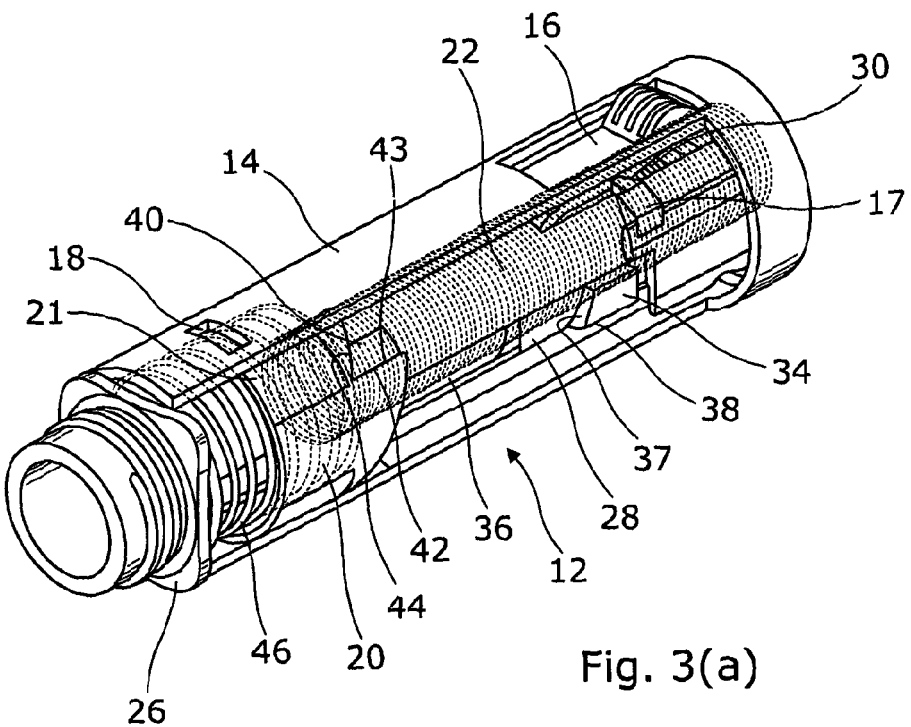
FIGS. 3 (*a*) to (*h*) are perspective views of the rear body assembly showing the configuration of various components in sequence through a firing and cocking operation, and FIGS. 4(*a*) to (*h*) are corresponding side views of the rear body assembly during these operations.
Figure 4A:
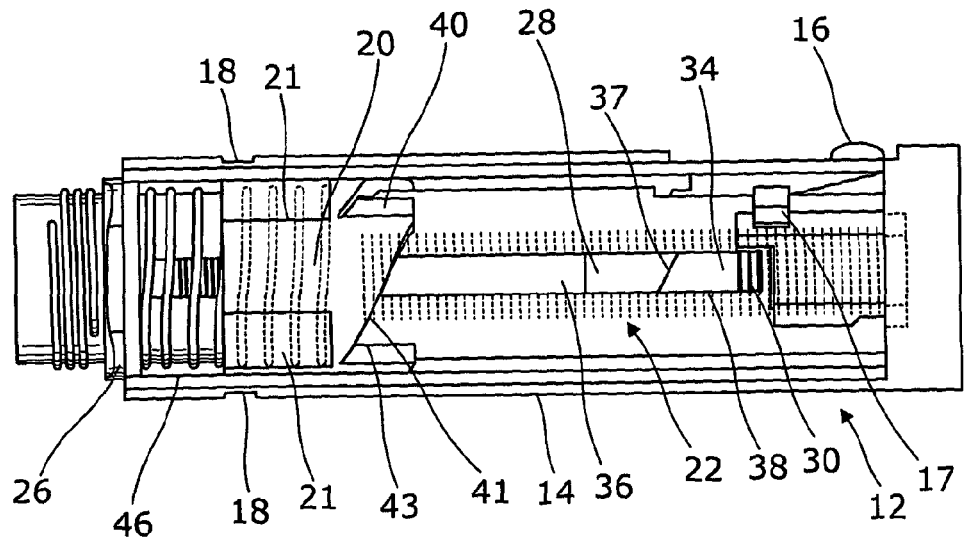

In operation, assuming the rear body assembly has been cocked, the components of the assembly will be as in the configuration shown in FIGS. 3(a) and 4(a). In this condition, the plunger 28 is latched in its cocked position with the main spring 30 fully compressed. The plunger ears 34 are at the rear of the slot 36. The indicator sleeve 20 is at its rearmost position urged by the spring 46 so that diametrically opposed valleys 45 of the saw tooth profile are urged into contact with the forward ends of the body stops 40, with the holding surfaces 42 of the body stops effectively urged into contact with the rising edges 43 of the saw tooth, by virtue of the cam surfaces 44 of the body stops 40 being in camming contact with the ramp surfaces 41 of the indicator sleeve 20. In this condition, the plain, uncoloured, surfaces of the indicator sleeve 20 are visible through windows 18.

Having prepared the device for injection and offered it up to an injection site and pressed the outer cover 14 to release the interlock with the trigger, the trigger 16 is pressed thereby releasing the drive plunger 28 so that it can shoot forward under the influence of the main drive spring 30, initially extending the syringe 22 so that its needle 24 projects from the front end of the front body assembly and thereafter moving the syringe piston 23 to expel a dose.

Figure 3B:
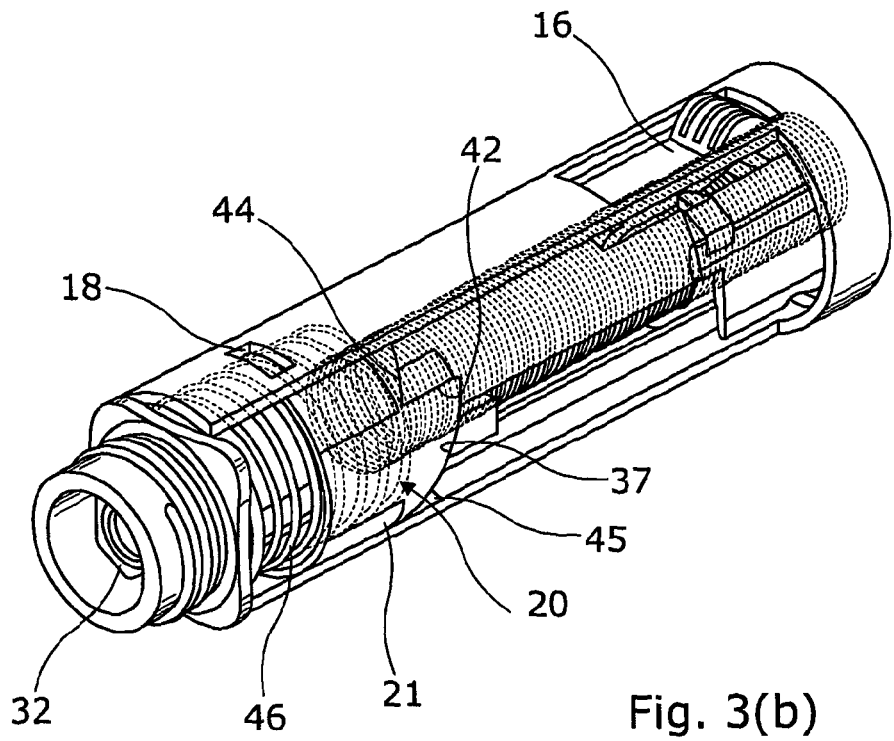
Figure 4B:
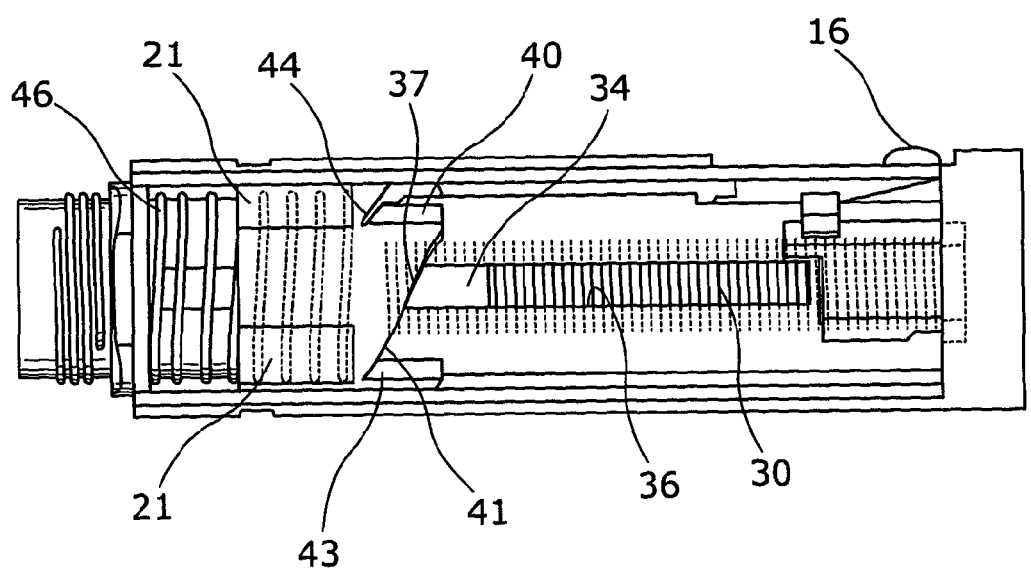
Figure 4C:
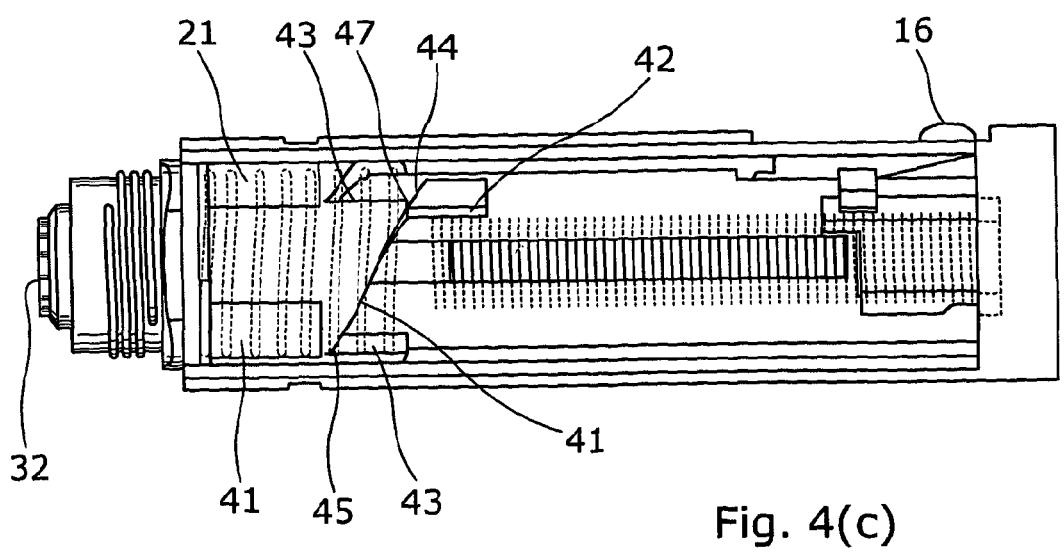

FIGS. 3(b) and 4(b) show the plunger having moved forward to the point where the cam surfaces 37 on the ears 34 of the plunger have just contacted respective ramp surfaces 41 on the indicator sleeve 20, but before any forward movement has been transmitted to the indicator sleeve. From this point, further forward movement of the plunger 28 shifts the indicator sleeve 20 against the bias of the spring 46, with the sleeve being constrained against rotation by the sliding contact between the holding surface 42 of the body stops and rising edges 43 of the indicator 20.

Figure 3C:
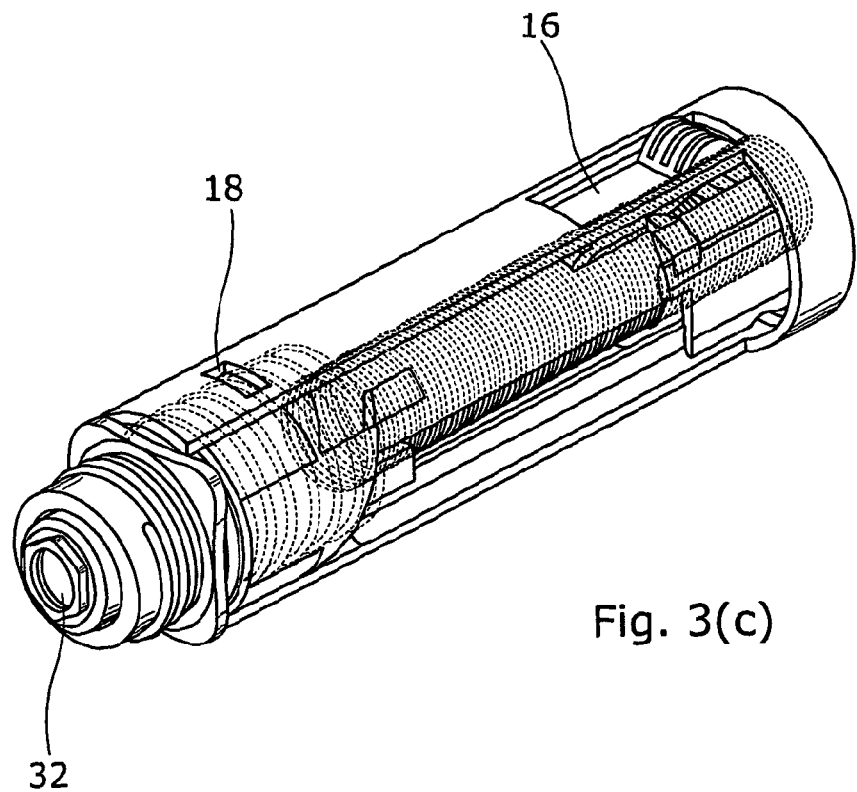
Figure 3D:
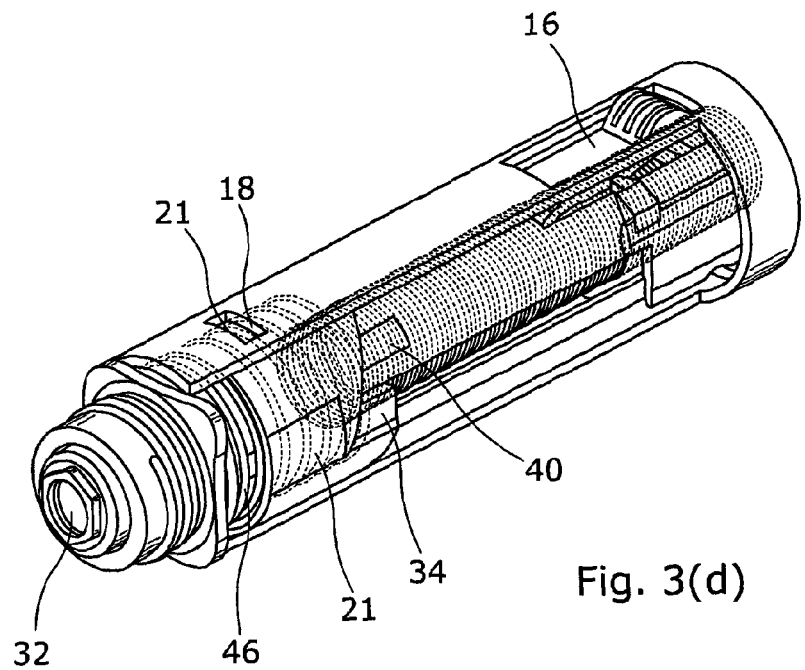
Figure 4D:
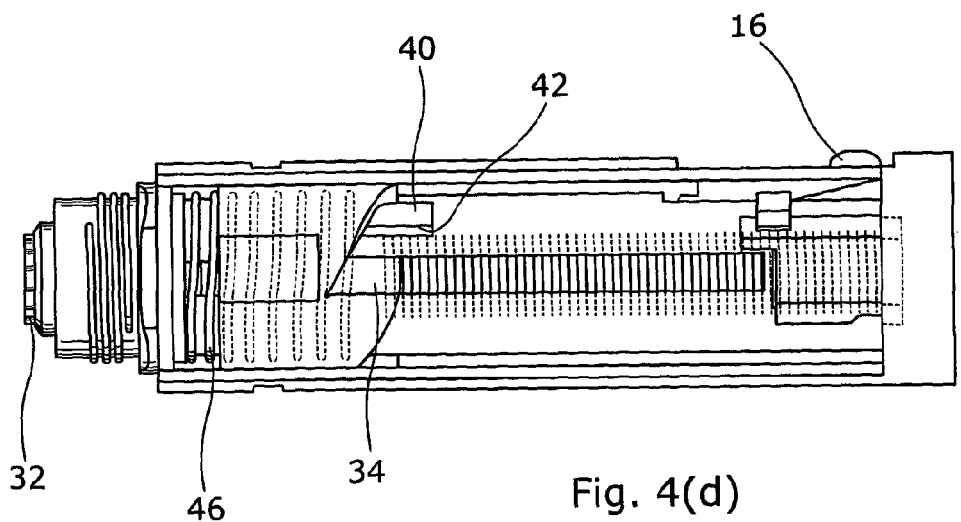
Figure 4E:
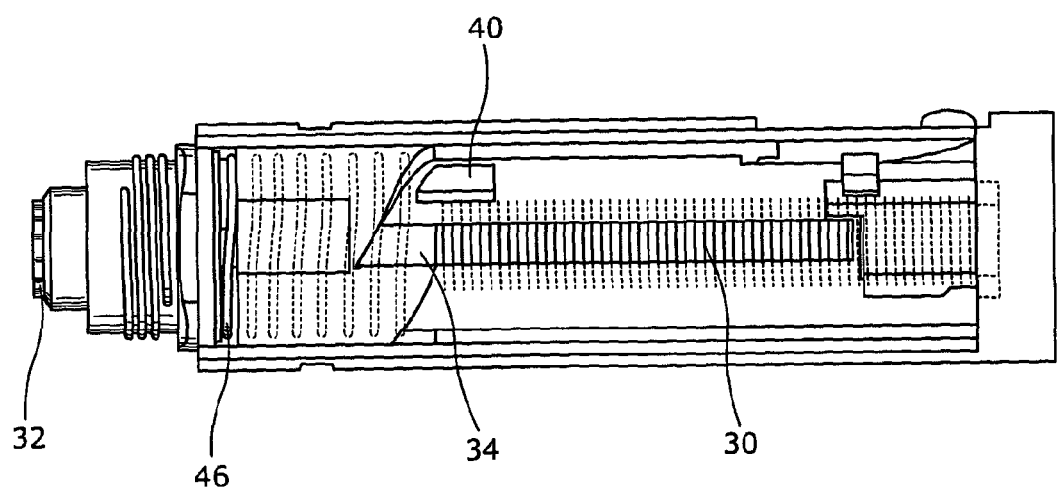

Beyond this point, as shown in FIGS. 3(d) and 4(d), the ramp surfaces 41 on the indicator 20 ride over the cam surfaces 37 and 44 on the plunger ears and body stops 40 respectively as the indicator sleeve 20 is now free to quickly rotate and move rearwardly under the influence of the expanding indicator spring 46 and the camming action of the ramps surfaces 41 on the cam surfaces 37, until the rising edges 43 on the indicator sleeve 20 impact the impact surfaces 38 on the ears 36, to generate an audible and tactile signal. At this point, the coloured region 21 on the indicator sleeve is now visible in the window 18 to indicate that the drive plunger 28 is at or near its forwardmost position. As noted above, due to the need to provide manufacturing tolerances due to the accumulated longitudinal tolerances in the syringe, the plunger continues moving forwardly a short distance to the position shown in FIGS. 3(e) and 4(e) which shifts the indicator sleeve 20 forwardly off the body stops 40.

Referring now to the cocking sequence shown in FIGS. 3 and 4(e) to (h), from a fully fired position, in order to cock the device, pressure is applied to the exposed end face 32 of the plunger to compress the main spring 30 e.g. using the forward end of the front body assembly 10 or other suitable tool and, as the plunger moves back, the indicator spring 46 expands to move the indicator sleeve 20 rearwardly with it.

Figure 3E:
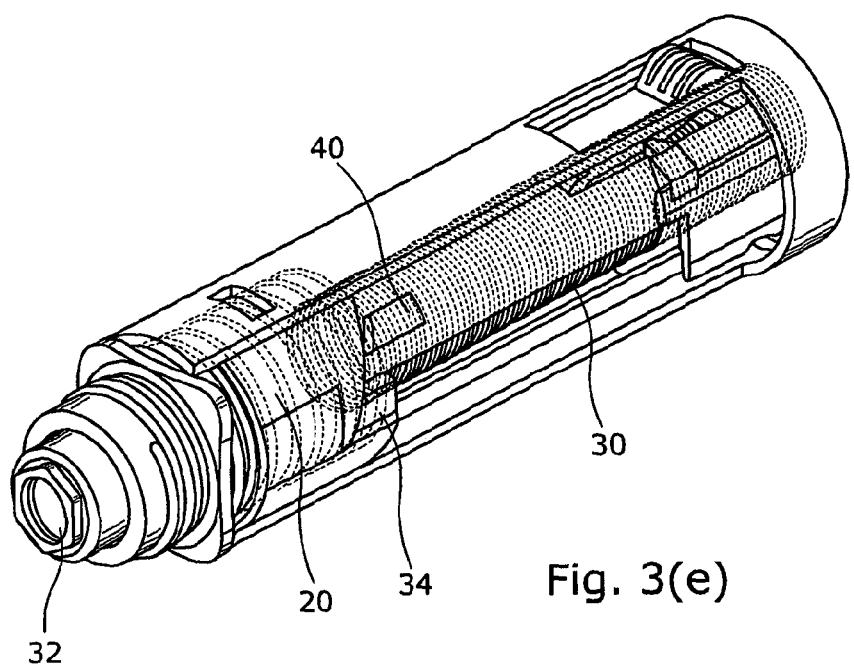
Figure 3F:
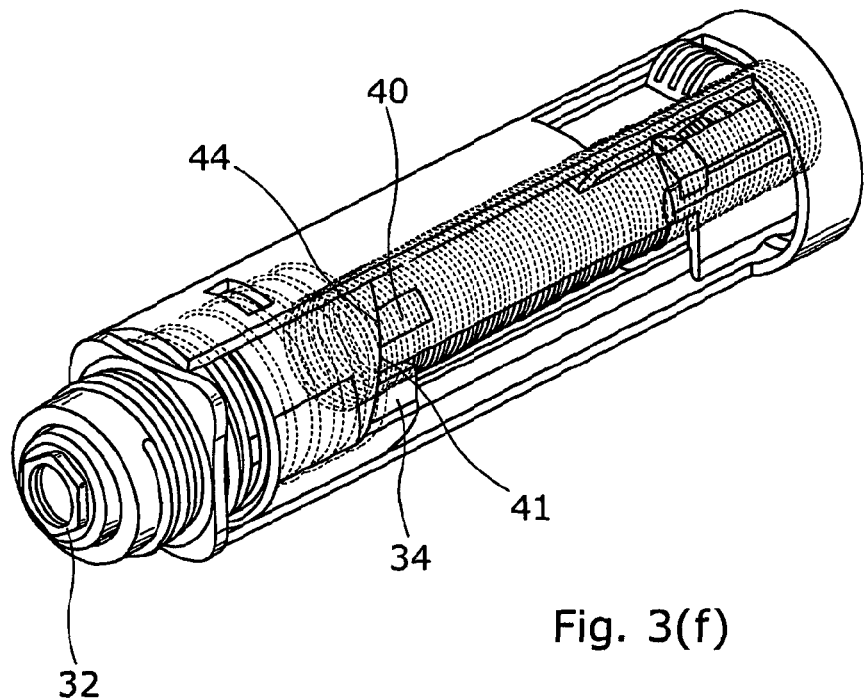
Figure 4F:
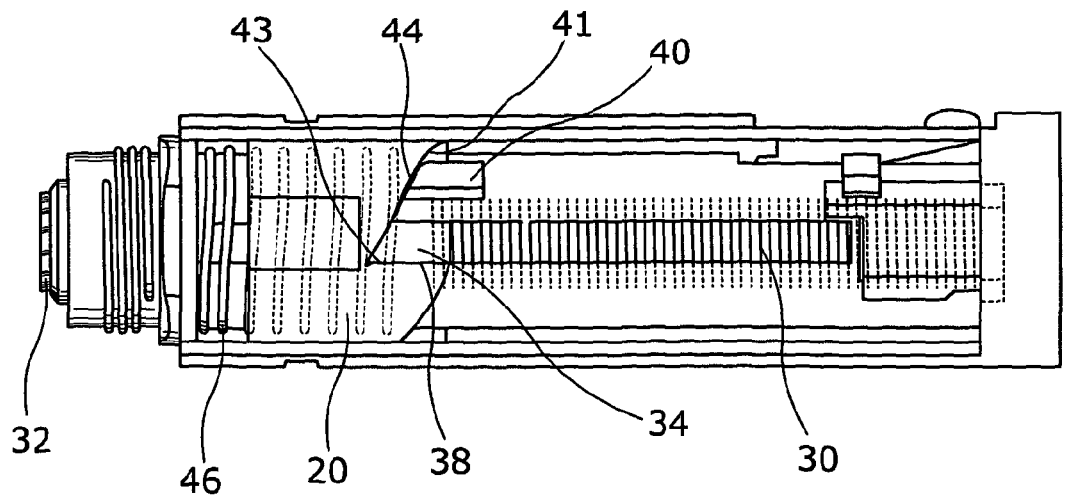
Figure 3G:
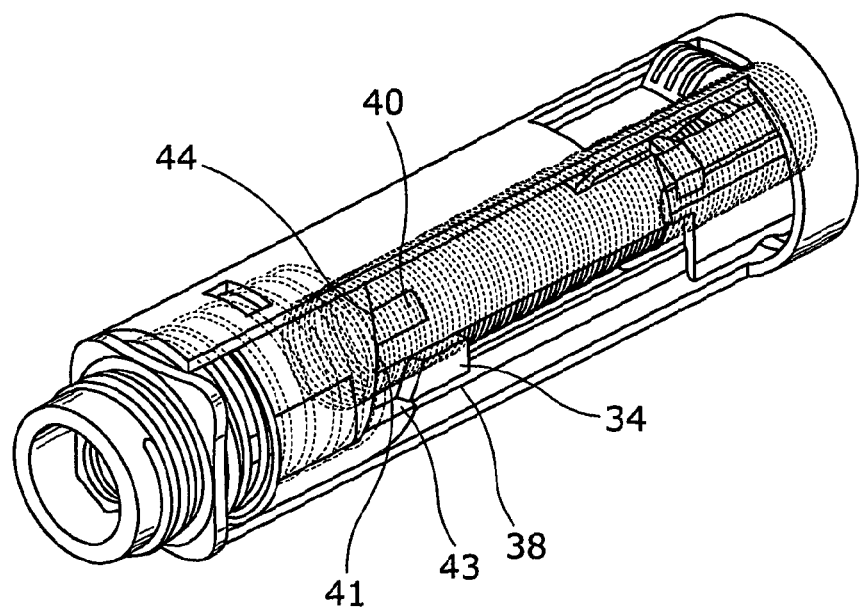
Figure 4G:
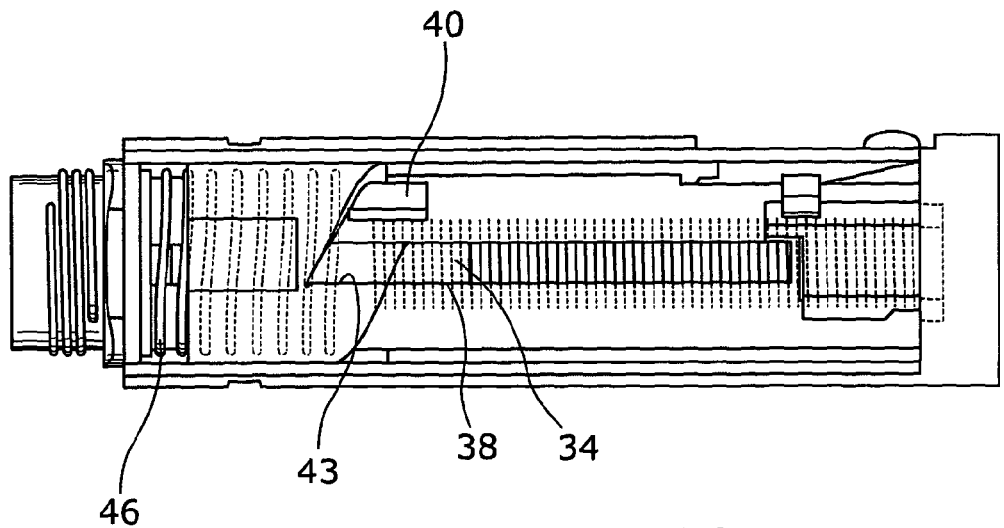
Figure 3H:
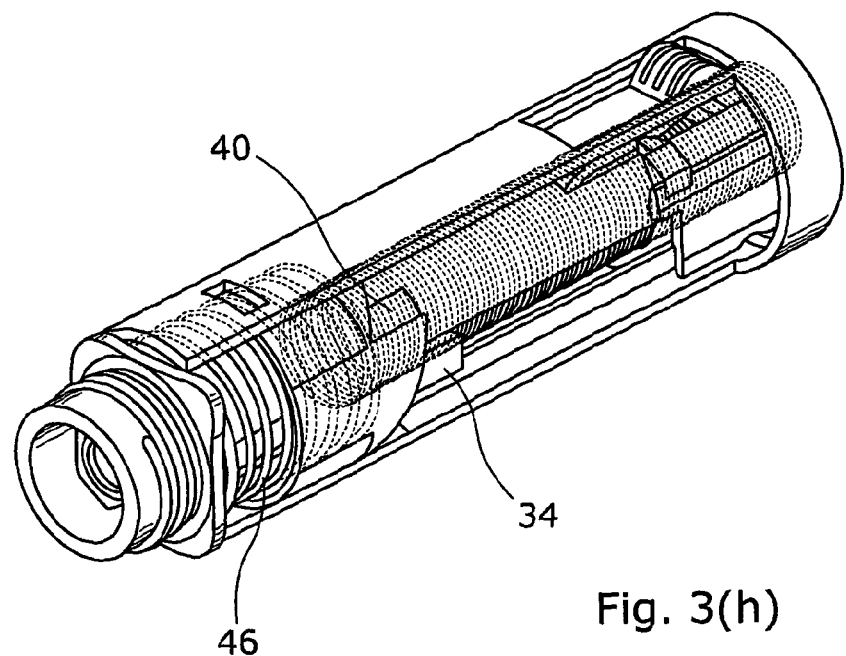
Figure 4H:
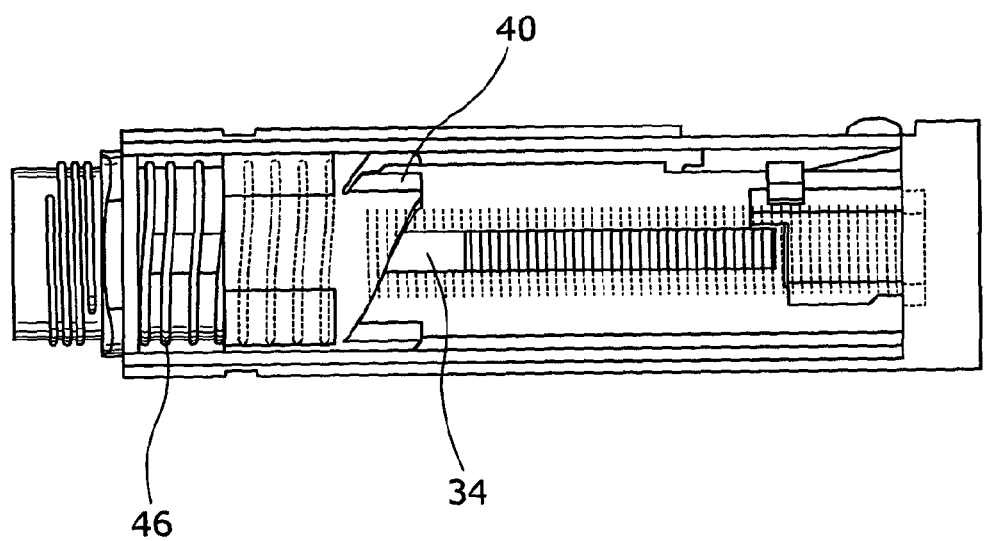

When the indicator sleeve 20 reaches the position shown in FIGS. 3(f) and 4(f) the ramp surfaces 41 thereon engage the cam surfaces 44 on the body stops 40, but rotational movement of the indicator sleeve 20 is prevented because of the sliding contact between the impact surface 38 of the ears 34 of the plunger and the rising edges 43 of the indicator sleeve 20. However, as shown in FIGS. 3(g) and 4(g), once the sliding contact is lost, the indicator sleeve 20 is free to rotate and consequently move rearwardly under the influence of the indicator compression spring 46 as the ramp surfaces 43 slide over the cam surfaces 44 of the body stops 40. This continues to the position shown in FIGS. 3(h) and 4(h), with the rising edges 43 of the indicator sleeve 20 abutting the holding surfaces 42 on the body stops 40. In this position the sleeve is located with an uncoloured portion visible through the window 18. Continued rearward movement of the plunger latches it against the trigger in the cocked position shown in FIGS. 3(a) and 4(a).

It will be noted that, in the embodiment described below, with each firing and cocking cycle, the indicator sleeve indexes through 90° (45° to move from the cocked, pre-firing state into the injection complete state and 45° in the same direction to move from the injection complete into the cocked state).

The invention claimed is:

1. An injection device including an injection complete indicator configured to provide both a visual indication and a kinetic impact indication, the device comprising:
a housing;
a plunger movable in said housing between cocked and fired positions under the influence of a plunger drive source;
an indicator element biased towards an injection complete indicating position by an indicator bias; and
a hold-release arrangement configured to hold the indicator element against the force of the indicator bias responsive to arrival of said plunger at or near the fired position to release said indicator element for movement under the influence of said indicator bias to move to said injection complete indicating position to impact a stop to create said kinetic impact and to provide a visual indication,
wherein as the plunger moves toward the fired position, the plunger energizes the indicator bias, and
the plunger and the indicator element have cooperating surfaces which engage to move the indicator element with the plunger during a portion of the plunger stroke to energize the indicator bias.

2. The injection device according to claim 1, wherein said hold-release arrangement includes a hold surface that cooperates with a complementary surface on said indicator element to prevent movement thereof to said injection complete indicating position during energization of said indicator bias.

3. The injection device according to claim 2, wherein as said plunger arrives near or at the fired position, the plunger moves the complimentary surface on the indicator element out of cooperation with said hold surface, thereby releasing the indicator element for movement.

4. The injection device according to claim 1, wherein said indicator element moves angularly to the injection complete indicating position.

5. An injection device including an injection complete indicator configured to provide both a visual indication and a kinetic impact indication, the device comprising:
a housing;
a plunger movable in said housing between cocked and fired positions under the influence of a plunger drive source;
an indicator element biased towards an injection complete indicating position by an indicator bias; and
a hold-release arrangement responsive to arrival of said plunger at or near the fired position to release said indicator element for movement under the influence of said indicator bias to move to said injection complete indicating position to impact a stop to create said kinetic impact and to provide a visual indication,
wherein the indicator bias biases the indicator element linearly in a direction generally opposed to that of the plunger as the plunger moves towards the fired position, and cooperating surfaces of said plunger and said indicator element act in a cammed manner to convert relative linear movement therebetween into angular movement of said indicator element.

6. The injection device according to claim 5, wherein the cooperating surfaces comprise an ear on said plunger and a repeating profile on said indicator element, the repeating profile comprising a plurality of ramp surfaces alternating with rising edge surfaces configured such that a rising edge surface is configured to impact a side of said ear as said indicator element reaches the injection complete indicating position.

7. The injection device according to claim 6, wherein said hold-release arrangement includes a hold surface that cooperates with a complementary surface on said indicator element to prevent movement thereof to said injection complete indicating position during energization of said indicator bias, and
wherein said hold surface is provided on an element that includes a cam face that cooperates with one of said ramp surfaces on said indicator element to rotate the indicator element to a pre-firing position under the influence of said indicator bias as said drive plunger is returned to a cocked position.

8. The injection device according to claim 2, wherein said indicator element moves angularly to the injection complete indicating position.

9. The injection device according to claim 3, wherein said indicator element moves angularly to the injection complete indicating position.

* * * * *